United States Patent
Roth et al.

(10) Patent No.: US 7,766,018 B2
(45) Date of Patent: Aug. 3, 2010

(54) DEVICE AND COMPOSITION FOR REDUCING THE INCIDENCE OF TOBACCO SMOKING

(75) Inventors: Brett J. Roth, Milwaukee, WI (US); Terrill S. Clayton, Wauwatosa, WI (US)

(73) Assignee: Smoke-Break, Inc., Madison, WI (US)

( * ) Notice: Subject to any disclaimer, the term of this patent is extended or adjusted under 35 U.S.C. 154(b) by 996 days.

(21) Appl. No.: 11/240,852

(22) Filed: Sep. 30, 2005

(65) Prior Publication Data
US 2006/0130857 A1 Jun. 22, 2006

Related U.S. Application Data

(60) Provisional application No. 60/614,883, filed on Sep. 30, 2004.

(51) Int. Cl.
*A24F 47/00* (2006.01)
(52) U.S. Cl. .............. 131/273; 131/271; 131/270; 131/352; 424/484; 424/487; 424/447; 128/200.21; 128/200.14; 604/89; 604/191; 604/218
(58) Field of Classification Search ............... None
See application file for complete search history.

(56) References Cited

U.S. PATENT DOCUMENTS

| | | | |
|---|---|---|---|
| 2,600,700 A | | 5/1952 | Smith |
| 3,076,456 A | * | 2/1963 | Hunt, Jr. .............. 604/89 |
| 3,845,217 A | | 10/1974 | Ferno et al. |
| 3,877,468 A | | 4/1975 | Lichtneckert et al. |
| 3,901,248 A | | 8/1975 | Lichtneckert et al. |
| 4,284,089 A | | 8/1981 | Ray |
| 4,429,703 A | | 2/1984 | Haber |
| 4,569,136 A | | 2/1986 | Loring |
| 4,806,356 A | | 2/1989 | Shaw |
| 4,813,437 A | | 3/1989 | Ray |
| 4,920,989 A | | 5/1990 | Rose et al. |
| 4,953,572 A | | 9/1990 | Rose et al. |
| 5,004,610 A | | 4/1991 | Osborne et al. |
| 5,110,605 A | | 5/1992 | Acharya |
| 5,147,654 A | | 9/1992 | Place et al. |

(Continued)

OTHER PUBLICATIONS

Simply Quit Cigarette Substitute—www.quitsmoking.com/simplyquit/index.htm.
E-Z Quit Artifical Cigarette—www.quitsmoking.com/ezquit/index.htm.
Triple Complex NicoTonic—www.nativeremedies.com/products/nicotonic-stop-smoking-naturally.html.

*Primary Examiner*—Philip C Tucker
*Assistant Examiner*—Phu H Nguyen
(74) *Attorney, Agent, or Firm*—Quarles & Brady, LLP

(57) ABSTRACT

A device which facilitates the absorption of nicotine in order to reduce the incidence of tobacco smoking is disclosed. The device includes a tube defining an interior space. The tube has a first end with an opening and a second end. An inhalable, flowable liquid or gel composition is disposed in the interior space of the tube. The composition may include water, at least one vitamin, a flavoring agent, and nicotine. The flavoring agent may include an intense sweetener such as sucralose, and a natural or artificial fruit flavor. A user inhales on the first end of the tube of the device as a substitute oral activity to tobacco smoking and thereby ingests a source of nicotine that reduces the withdrawal symptoms experienced when smoking is stopped.

20 Claims, 5 Drawing Sheets

U.S. PATENT DOCUMENTS

| | | |
|---|---|---|
| 5,167,242 A | 12/1992 | Turner et al. |
| 5,326,563 A | 7/1994 | Spindler et al. |
| 5,358,970 A | 10/1994 | Ruff et al. |
| 5,400,808 A | 3/1995 | Turner et al. |
| 5,496,288 A * | 3/1996 | Sweeney .................... 604/263 |
| 5,501,236 A | 3/1996 | Hill et al. |
| 5,549,906 A | 8/1996 | Santus |
| 5,633,008 A | 5/1997 | Osborne et al. |
| 5,656,255 A | 8/1997 | Jones |
| 5,779,668 A * | 7/1998 | Grabenkort .................. 604/89 |
| 5,799,663 A | 9/1998 | Gross et al. |
| 5,810,018 A | 9/1998 | Monte |
| 6,098,632 A | 8/2000 | Turner et al. |
| 6,102,036 A | 8/2000 | Slutsky et al. |
| 6,106,845 A * | 8/2000 | Wong et al. .................. 424/400 |
| 6,165,497 A | 12/2000 | Osborne et al. |
| 6,211,194 B1 | 4/2001 | Westman et al. |
| 6,248,760 B1 | 6/2001 | Wilhelmsen |
| 6,268,386 B1 | 7/2001 | Thompson |
| 6,410,550 B1 | 6/2002 | Coe et al. |
| 6,412,494 B1 | 7/2002 | Bloom, Jr. |
| 6,479,076 B2 * | 11/2002 | Blank ......................... 424/484 |
| 6,769,436 B2 | 8/2004 | Horian |
| 6,893,654 B2 | 5/2005 | Pinney et al. |
| 7,115,297 B2 | 10/2006 | Stillman |
| 2002/0059939 A1 | 5/2002 | Fox |
| 2003/0084912 A1 * | 5/2003 | Pera .......................... 131/352 |
| 2003/0111088 A1 | 6/2003 | Fox |
| 2006/0191546 A1 | 8/2006 | Takano et al. |

\* cited by examiner

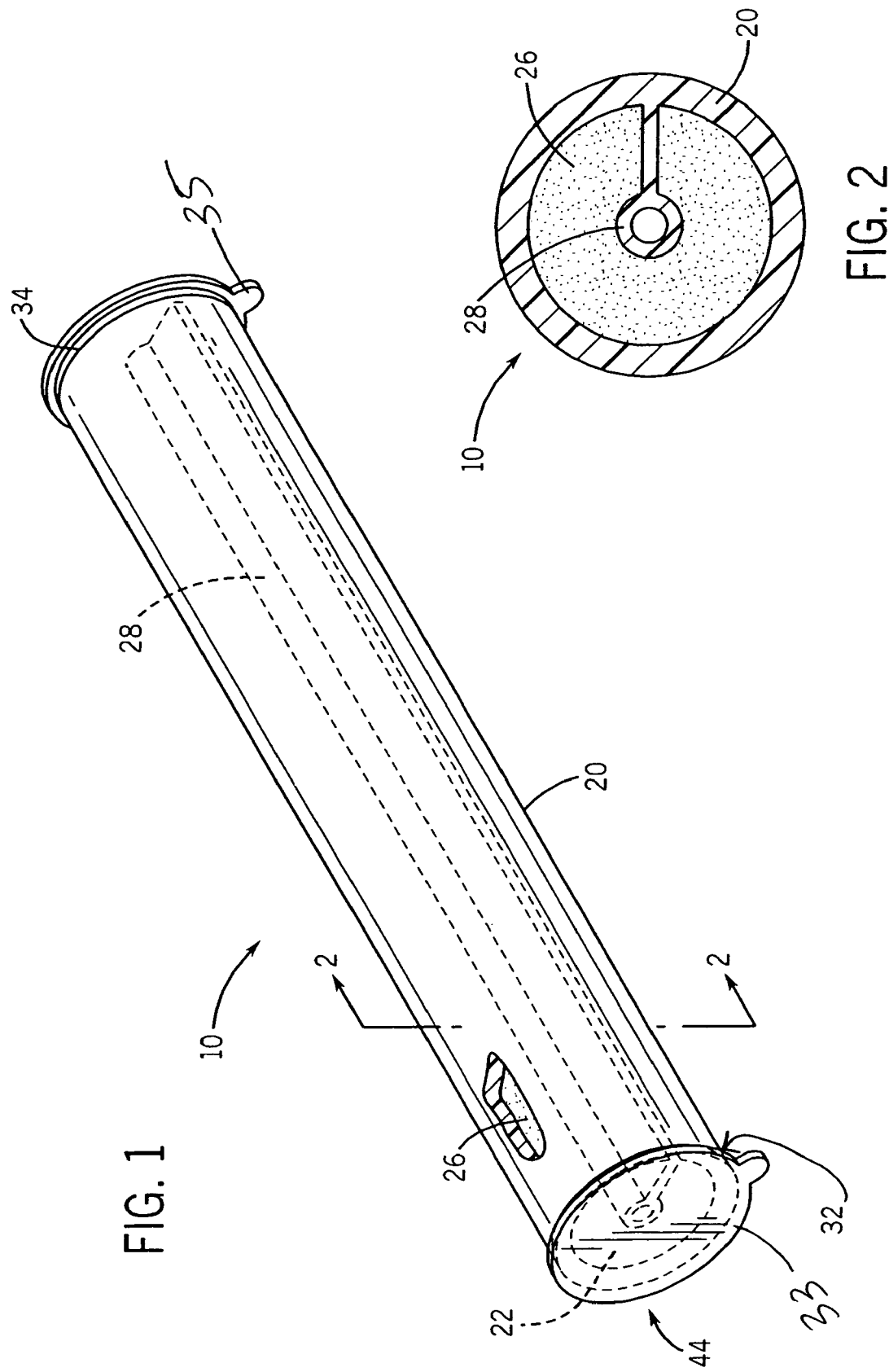

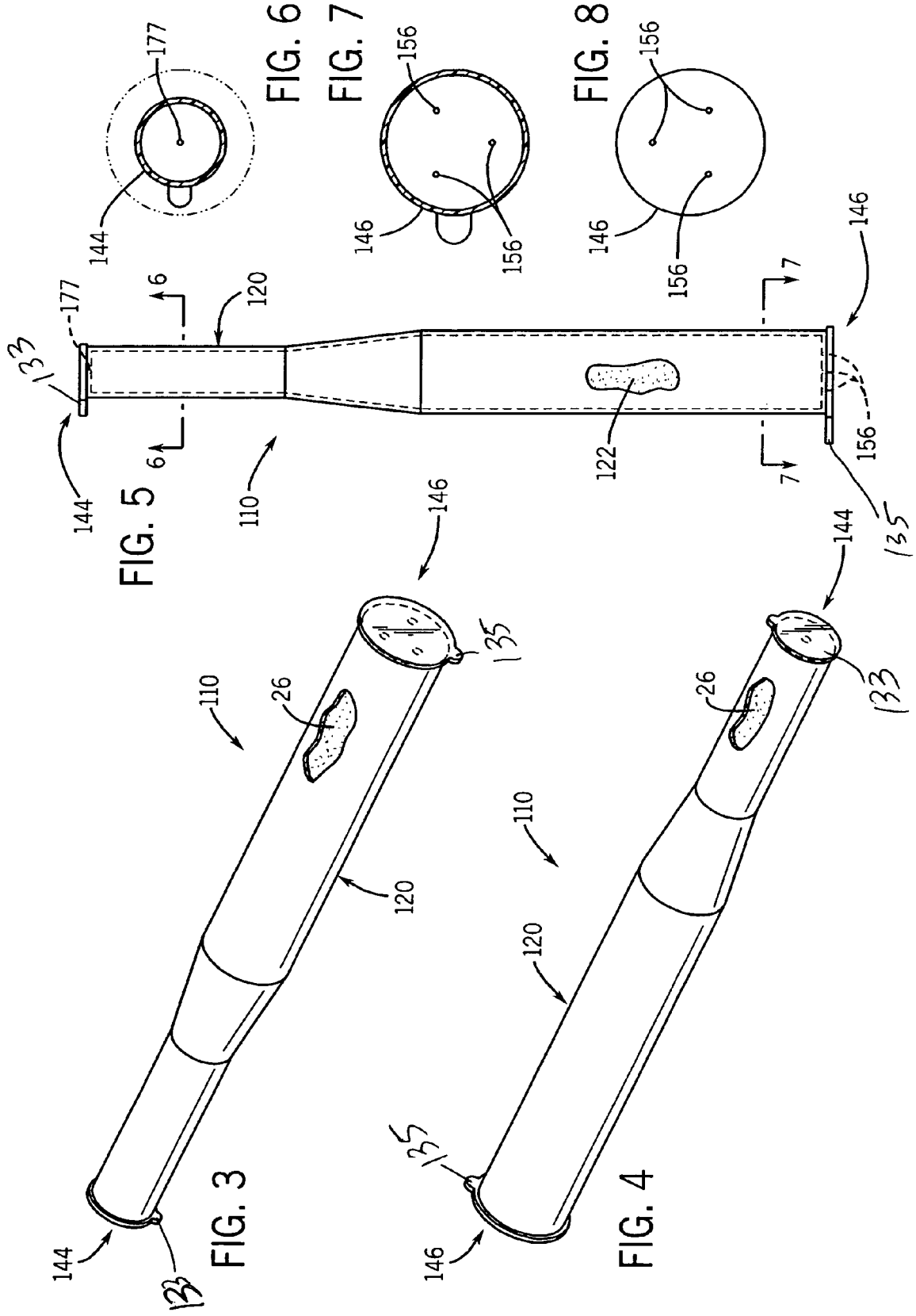

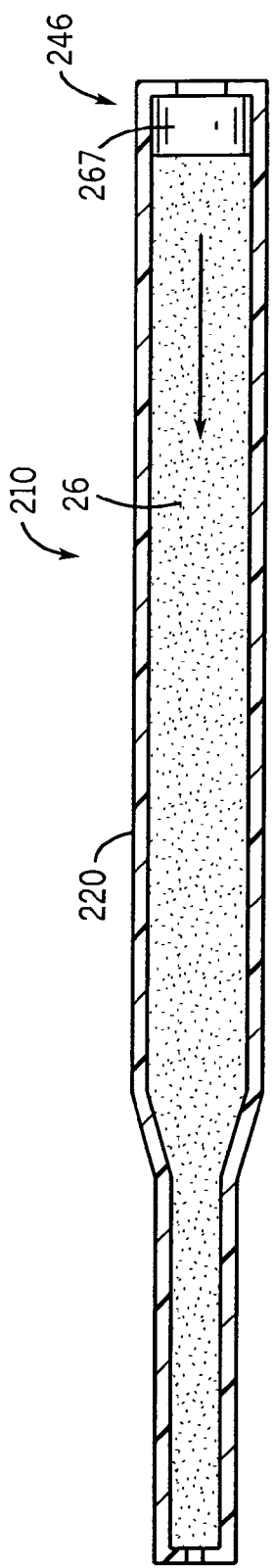
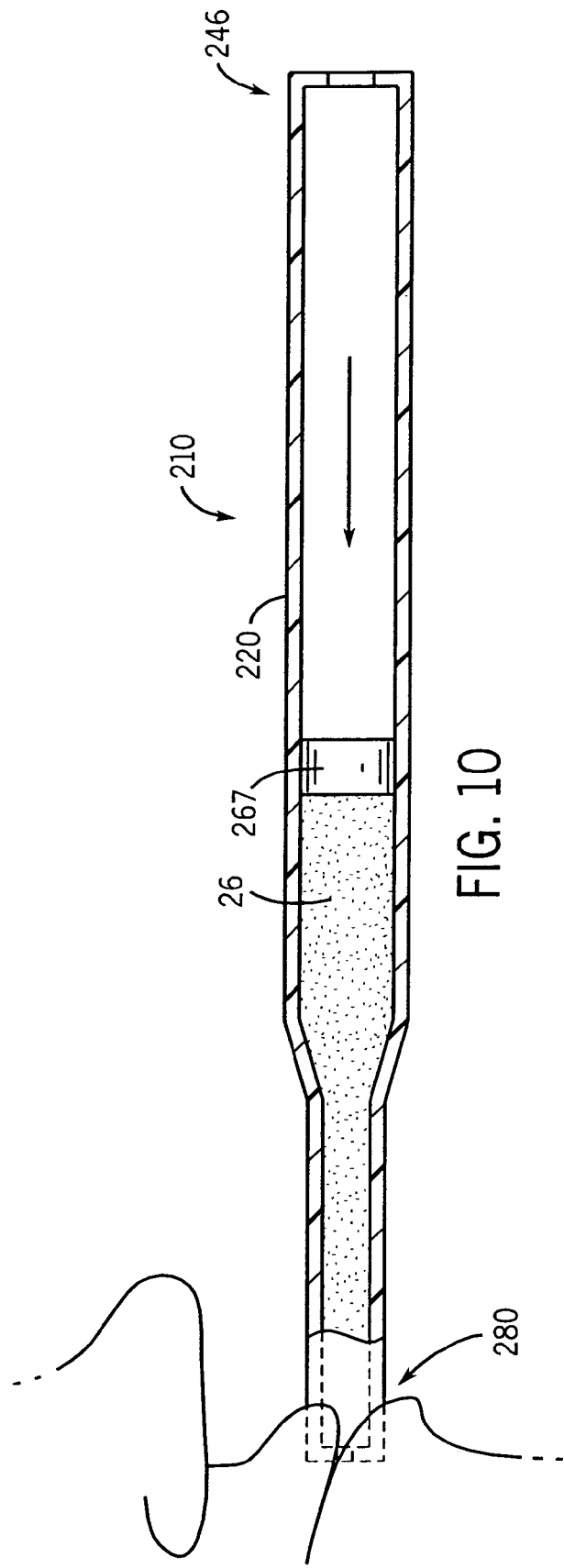

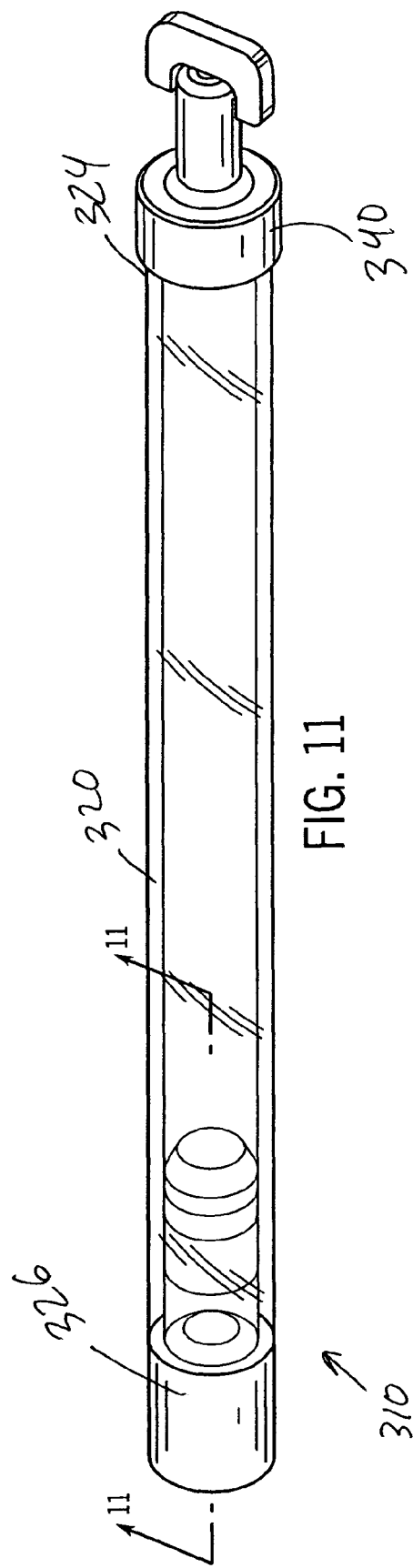
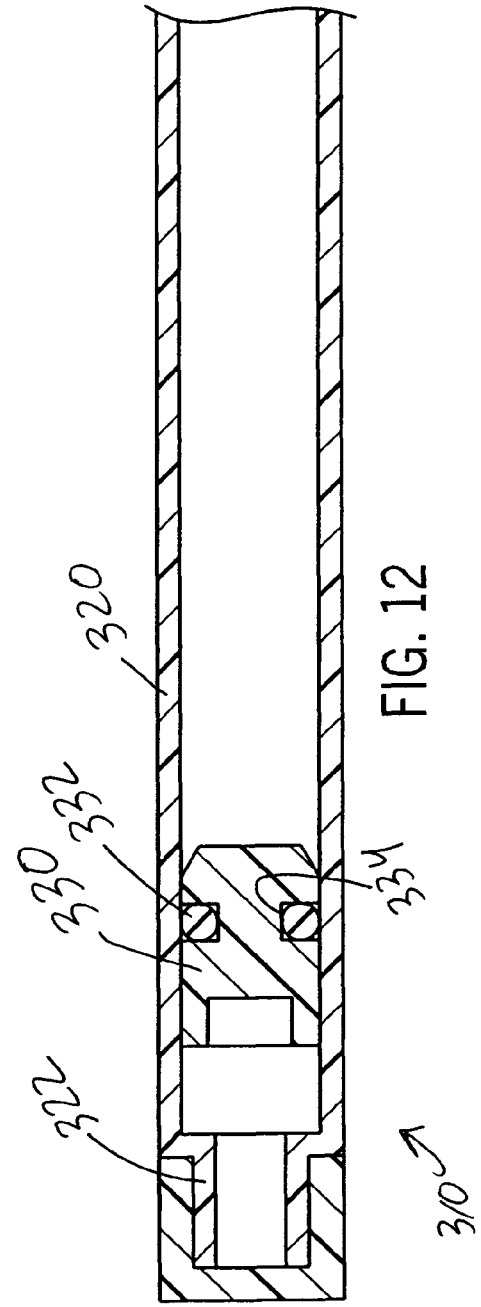
FIG. 11
FIG. 12

DEVICE AND COMPOSITION FOR REDUCING THE INCIDENCE OF TOBACCO SMOKING

CROSS-REFERENCES TO RELATED APPLICATIONS

This application claims priority from U.S. Provisional Patent Application No. 60/614,883 filed Sep. 30, 2004.

STATEMENT REGARDING FEDERALLY SPONSORED RESEARCH

Not Applicable.

BACKGROUND OF THE INVENTION

1. Field of the Invention

This invention relates to a device, method and composition for reducing the incidence of tobacco smoking. More particularly, the invention relates to a device, composition, and method which facilitate the absorption of nicotine in order to reduce the incidence of tobacco smoking.

2. Description of the Related Art

Nicotine is an addictive alkaloid derived from the tobacco plant. When smoking a cigarette, nicotine is quickly absorbed into the smoker's blood and reaches the brain within eight seconds after inhalation. With the increasing recognition of the health hazards associated with the smoking of tobacco, increasing attention has been focused on less harmful means to provide some of the satisfaction obtained by smoking. By giving the smoker an alternative source of nicotine, smoking withdrawal symptoms can be relieved and smoking abstinence facilitated.

In nicotine replacement therapy, one alternative source of nicotine is nicotine chewing gum or a nicotine lozenge. However, one disadvantage with these products is that many users dislike the taste of these products. Also, these products do not closely resemble the act of smoking a lit cigarette.

Another alternative source of nicotine is a nicotine skin patch. However, these products do not deliver a dose of nicotine directly to the mucous membrane of the mouth or lungs where it is absorbed quickly and transferred to the brain to satisfy the craving for nicotine. Also, these products do not closely resemble the act of smoking a lit cigarette. Furthermore, the patches may cause skin irritation.

Yet another alternative source of nicotine is nicotine nasal or oral sprays. However, nasal sprays may produce sneezing and tearing, and oral sprays may have an unpleasant taste.

Still another alternative source of nicotine is nicotine inhalers which deliver nicotine vapor or gases through inhalation to the user without damaging smoke. One advantage to inhalers is that they more closely resemble the act of smoking. Such inhalers deliver a dose of nicotine directly to the mucous membrane of the mouth and/or lungs where it is absorbed quickly and transferred to the brain to satisfy the craving for nicotine. Another advantage to nicotine inhalers is that they can be made in a similar shape and size to that of a cigarette to more closely resemble the act of smoking a lit cigarette. Additionally, inhalers can provide the "hit" upon demand of a sudden dose of delivered nicotine to the user that is similar to a lit cigarette. However, they have a major disadvantage in that the nicotine inhalers may produce a burning sensation in the throat. Also, nicotine inhalers can be quite expensive. In addition, certain vitamins that are decreased by smoking cannot be delivered in the vapor phase.

Therefore, there is a continuing need for a nicotine replacement product that resembles the act of smoking a cigarette and that has an acceptable taste.

BRIEF SUMMARY OF THE INVENTION

The foregoing needs are met by the present invention which provides a device, composition and method which facilitate the absorption of nicotine in order to reduce the incidence of tobacco smoking.

In one aspect, the invention provides a device which facilitates the absorption of nicotine in order to reduce the incidence of tobacco smoking. The device includes a tube defining an interior space. The tube has a first end with an opening and a second end. An inhalable, flowable liquid or gel composition is disposed in the interior space of the tube. The composition includes nicotine, and the composition is formulated to be suitable to enter a user's mouth through the opening in the first end when the user inhales through the first end of the tube of the device.

In one form, the device has an air tube positioned in the interior space of the tube and the air tube is free from the composition. The air tube provides an air flow path in the device. The first end and the second end of the device may be covered with a removable seal. Preferably, the amount of composition in the interior space of the tube is approximately 3 to 20 milliliters, and the amount of nicotine in the interior space of the tube is 0.5 to 5.0 milligrams. The composition may include a vitamin and a flavoring agent. For example, the flavoring agent may include sucralose, and a natural or artificial fruit flavor. The vitamin may be selected from vitamin C, vitamin E, Vitamin B, and mixtures thereof, and the flavoring agent may include a natural or artificial fruit flavor selected from cherry, orange, grape, root beer, cola, spearmint and menthol.

In another form, the second end of the device is moveable such that the second end may move toward the user's mouth upon the user inhaling through the first end. As a result, all of the composition is delivered to the user, i.e., nothing would be left on the inner sides of the tube. In still another form of the device, the second end is integral with the tube and includes at least one air hole. In yet another form, the first end of the device is a porous membrane. Optionally, the tube has indicia on the first end of the tube to indicate where the user should inhale. Preferably, the first end is covered with a mouthpiece having a frangible seal.

In another aspect, the invention provides an inhalable, flowable composition which facilitates the absorption of nicotine in order to reduce the incidence of tobacco smoking. The composition includes water, at least one vitamin, a flavoring agent, and nicotine. The vitamin may be selected from vitamin C, vitamin E, Vitamin B, and mixtures thereof. The flavoring agent may include an intense sweetener such as sucralose, and a natural or artificial fruit flavor. Preferably, the composition includes a thickener such that the composition is a gel, and the composition further includes a preservative.

In yet another aspect, the invention provides a method which facilitates the absorption of nicotine in order to reduce the incidence of tobacco smoking. The method includes providing a device that includes a tube defining an interior space wherein the tube has a first end with an opening and a second end. An inhalable, flowable liquid or gel composition is disposed in the interior space of the tube. The composition includes nicotine, and the composition is formulated to be suitable to enter a user's mouth through the opening in the first end when the user inhales through the first end of the tube of the device. A user inhales on the first end of the tube of the device as a substitute oral activity to tobacco smoking and thereby ingests a source of nicotine that reduces the withdrawal symptoms experienced when smoking is stopped. Thus, the method facilitates the absorption of nicotine in order to reduce the incidence of tobacco smoking.

In still another aspect, the invention provides a method which facilitates the absorption of nicotine in order to reduce the incidence of tobacco smoking. The method includes the step of administering a composition according to the invention to a user's mouth. The composition includes water, at least one vitamin, a flavoring agent, and nicotine. The vitamin may be selected from vitamin C, vitamin E, Vitamin B, and mixtures thereof. The flavoring agent may include an intense sweetener such as sucralose, and a natural or artificial fruit flavor. Preferably, the composition includes a thickener such that the composition is a gel, and the composition further includes a preservative.

Thus, it is an advantage of the present invention to provide a nicotine replacement product that resembles the act of smoking a cigarette and that has an acceptable taste.

It is another advantage of the present invention to provide a device which facilitates the absorption of nicotine in order to reduce the incidence of tobacco smoking and also delivers a vitamin to the user.

It is another advantage of the present invention to provide an oral composition which provides a source of nicotine that reduces the withdrawal symptoms experienced when smoking is stopped.

These and other features, aspects, and advantages of the present invention will become better understood upon consideration of the following detailed description, drawings, and appended claims.

BRIEF DESCRIPTION OF THE DRAWINGS

FIG. 1 is a perspective view of a first embodiment of a device according to the invention.

FIG. 2 is a cross-sectional view of the device of FIG. 1 taken along line 2-2 of FIG. 1.

FIG. 3 is a front left perspective view of a second embodiment of a device according to the invention.

FIG. 4 is a rear right perspective view of the device of FIG. 3.

FIG. 5 is a side elevational view of the device of FIG. 3.

FIG. 6 is a cross-sectional view of the device of FIG. 5 taken along line 6-6 of FIG. 5.

FIG. 7 is a cross-sectional view of the device of FIG. 5 taken along line 7-7 of FIG. 5.

FIG. 8 is a front elevational view of the device of FIG. 3 with the shipping seal removed.

FIG. 9 is a cross-sectional side view of a third embodiment of a device according to the invention.

FIG. 10 is a view similar to FIG. 9 during use of the device.

FIG. 11 is a rear right perspective view of a fourth embodiment of a device according to the invention.

FIG. 12 is a cross-sectional view of the device of FIG. 11 taken along line 11-11 of FIG. 11.

Like reference numerals will be used to refer to like parts from Figure to Figure in the following description of the drawings.

DETAILED DESCRIPTION

Figure 14:
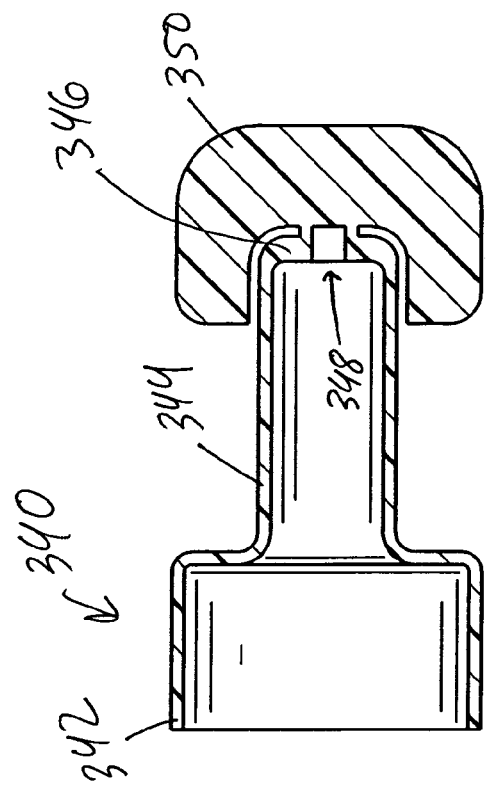
FIG. 14 is a cross-sectional view of the cap of FIG. 13 taken along line 14-14 of FIG. 13.

Turning to FIG. 1, there is shown a first embodiment of a device 10 according to the invention which facilitates the absorption of nicotine in order to reduce the incidence of tobacco smoking. Shaped like a cigarette or small cigar, the dimensions of an example of the device (which can be called a "dispenser") are as follows, but shall not limited to: 9.5 centimeters long, 1 centimeter outside diameter and cylindrical (about 3 centimeters circumference), with a wall thickness of 0.1 centimeters. The color of the cigarette-like product will be, but shall not be limited to, brown, so that it resembles a small blunt, or cigarillo. It may also be designed to be white, with an imitation filter. Plastic is a suitable material for the device.

The device 10 has an outer cylindrical tube 20 and inside the tube 20, there may be a chamber 22 defining an interior space which will carry a composition 26 according to the invention. A central air tube 28 of variable size is centered in the chamber 22. The air tube 28 is optional, and may not be included in the device. In other words, the device may only include a single chamber 22. The amount of composition inside of the tube can be, but is not limited to, approximately 3-5 milliliters, with one version having a volume of 4.77 milliliters excluding the air tube 28.

On the "mouth" end of the tube 20 there is a porous membrane 32, or filter, which will allow the user to inhale, or sip, the composition 26. The other end will have a non-porous membrane, or filter 34, or may be sealed off with the material that comprises the tube 20. A seal 33, of aluminum foil or comparable substance, can be used to seal the mouth end of the dispensing tube 20, and a seal 35, of aluminum foil or comparable substance, can be used to seal the opposite end of the dispensing tube 20 to preserve freshness, and to prevent accidental ingestion by toddlers. To use the device 10, the user will have to remove the foil on each end.

The user will have an amount of control over the volume of composition received in a "dose." He or she may inhale lightly, or hardly at all, to receive a minimal amount of composition 26. He or she may inhale naturally, or normally, to receive a single "dose," approximately 0.35 ml. of composition 26. He or she may inhale deeply to receive a double, or triple "dose," approximately 0.7 ml-1.05 ml. The product shall only be designed to imitate, and therefore replace, the act of smoking. Thus, the device provides a nicotine replacement product that resembles the act of smoking a cigarette.

The tube 20 will be disposable, and should be discarded into a trash receptacle after usage. The device will be sold individually, in packs or cartons, similar to cigarettes, and shall contain, but shall not be limited to, 15-20 individual devices, or "cigarettes." The packs may be opened in the same manner as cigarette packs and cartons. In another version, the tube 20 is refillable with the composition.

A marking on the "mouth" end 44 of the tube 20 can signify to the user that this is the end he/she should inhale. A larger, cigar-like version of this device 10 may also be produced and the composition 26 can be adjusted to be a different volume, viscosity, and concentration, so as to be delivered in any smoking-imitative way.

Turning to FIGS. 3-8, there is shown a second embodiment of a device 110 according to the invention which facilitates the absorption of nicotine in order to reduce the incidence of tobacco smoking. Shaped like a cigarette or small cigar, the dimensions of the device 110 (which can be called a "dispenser") are as follows, but shall not limited to: 110 millimeters long, with a wall thickness of 0.5 millimeters. It is substantially cylindrical. The device 110 has an outside diameter of 8.5 millimeters from the mouth end 144 to about 30 millimeters from the mouth end 144, and the outside diameter then increases from 8.5 millimeters to 12 millimeters from 30 to 50 millimeters from the mouth end 144. Thus, the outside diameter on the opposite end 146 is 12 millimeters. The color of the cigarette-like product will be, but shall not be limited to, brown, so that it resembles a small blunt, or cigarillo. It may also be designed to be white, with an imitation filter. Plastic is a suitable material for the device 110.

Inside the tube 120, there is a chamber 122 which will carry the composition 26 according to the invention The amount of composition inside of the tube can be, but is not limited to, approximately 6-9 milliliters.

A seal 133, of aluminum foil or comparable substance, can be used to seal the mouth end 144 of the dispensing tube 120, and a seal 135, of aluminum foil or comparable substance, can be used to seal the opposite end 146 of the dispensing tube 120 to preserve freshness, and to prevent accidental ingestion by toddlers. To use the device 110, the user will have to remove the foil on each end.

Both ends are sealed off with the same plastic material as the rest of the tube. On the mouth end 144 of the tube 120 there is a single hole 177 (see FIG. 6), approximately 0.8 millimeters in diameter, where the use may inhale the composition 26. On the other end 146 of the tube 120 there are three air holes 156 (see FIGS. 7-8), approximately 0.38 millimeters in diameter each, to facilitate air flow into the tube 120. The air holes 156 are equally spaced in a 6 millimeter diameter circle.

Alternatively, the "mouth" end 144 of the tube 120 may have a porous membrane, which will allow the user to inhale, or sip, the composition 26. The other end 146 may have a non-porous membrane.

The user will have an amount of control over the volume of composition received in a "dose." He or she may inhale lightly, or hardly at all, to receive a minimal amount of composition 26, approximately 0.20-0.60 milliliters of the composition 26. He or she may inhale naturally, or normally, to receive a single "dose," approximately 0.1.0 ml. of composition 26. He or she may inhale deeply to receive a double, or triple "dose," approximately 2.0 ml. The product shall only be designed to imitate, and therefore replace, the act of smoking. Thus, the device provides a nicotine replacement product that resembles the act of smoking a cigarette.

The tube 120 will be disposable, and should be discarded into a trash receptacle after usage. The device will be sold individually, in packs or cartons, similar to cigarettes, and shall contain, but shall not be limited to, 15-20 individual devices, or "cigarettes." The packs will open in the same manner as cigarette packs and cartons.

A marking on the "mouth" end 144 of the tube 120 can signify to the user that this is the end he/she should inhale. A larger, cigar-like version of this device may also be produced and the composition can be adjusted to be a different volume, viscosity, and concentration, so as to be delivered in any smoking-imitative way.

Turning to FIGS. 9 and 10, there is shown a third embodiment of a device 210 according to the invention which facilitates the absorption of nicotine in order to reduce the incidence of tobacco smoking. The device is similar to the device 110 of FIGS. 3-8. However, the end 246 of the device 210 includes a moveable plug 267. Designed much like a syringe without the plunger, the plug 267 moves from the other (far) end 246 of the tube 220 to the "mouth" end 280, as the user inhales. An advantage of this system would be that all fluid would be delivered to the user, i.e., nothing would be left on the inner sides of the tube 220.

Referring now to FIGS. 11-14, there is shown a fourth embodiment of a device 310 according to the invention which facilitates the absorption of nicotine in order to reduce the incidence of tobacco smoking. The device 310 has a hollow cylindrical tube 320 with a reduced diameter (far) end 322 and a "mouth" end 324. An end cap 326 fits over the end 322 to seal off the end 322. The device 310 includes a plug 330 that moves from the end 322 of the tube 320 to the mouth end 324 of the tube 324. The plug 330 has an O-ring 332 in an annular surface channel 334 of the plug 330. A mouthpiece 340 covers the mouth end 324 of the device 310. In one version, the tube 324 has an outside diameter of 0.375 inches and the device 310 has an overall length of 5 inches. Preferably, the device 310 holds about 9 milliliters of the composition 26. However, the size of the tube can be increased to allow for more fluid space, such as 20 milliliters. The tube may be clear, translucent or opaque, and may be colored brown like a cigar.

Figure 13:
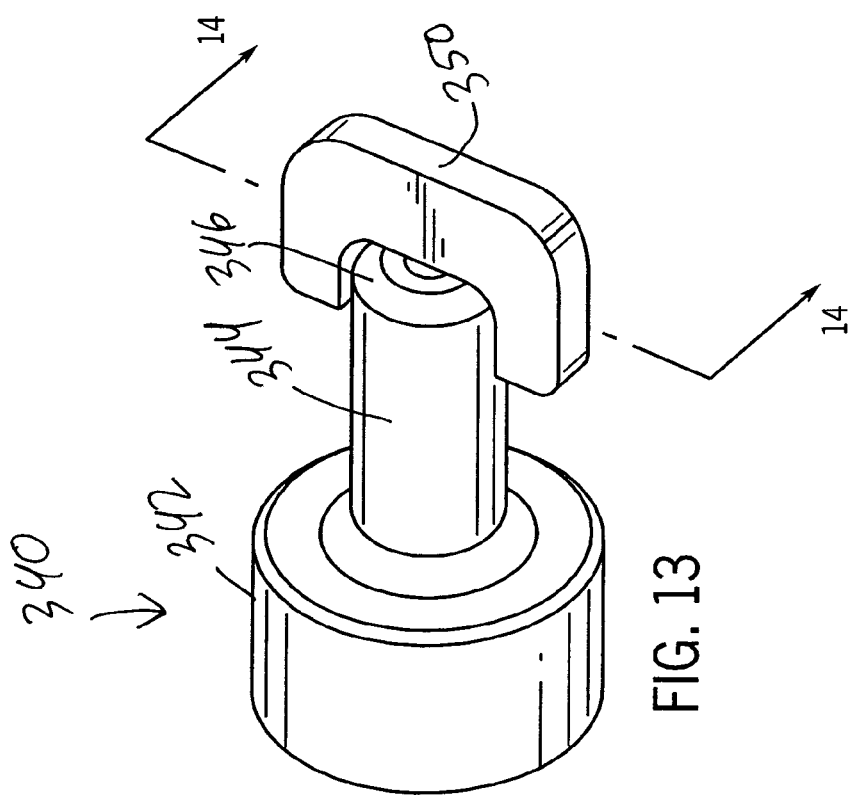
FIG. 13 is a perspective view of the cap of the device of FIG. 11.

Looking at FIGS. 13 and 14, the mouthpiece 340 has a first hollow tubular end 342 that fits over the mouth end 324 to seal off the mouth end 324. The mouthpiece 340 also has a central hollow tubular section 344 of reduced outside diameter in relation to the tubular end 342. The central hollow tubular section 344 has an end wall 346 with a central opening 348. Before use, the central opening 348 is sealed off by a tear-away tab 350. By twisting the tear-away tab 350, the user breaks off section 352 of the mouthpiece 340 creating a flow path from central opening 348 to tubular section 344 to tubular end 342 of the mouthpiece 340. Thus, the tab 350 serves as a frangible seal. As a user inhales on the tubular section 344 of the mouthpiece 340 of the device 310 to receive composition 26 from the device 310, the plug 330 moves from the far end 322 of the tube 320 to the mouth end 324. An advantage of this system would be that all fluid would be delivered to the user, i.e., nothing would be left on the inner sides of the tube 320.

The composition 26 loaded into the device 10 or 110 or 210 or 310 may contain, but shall not be limited to, the following ingredients: distilled water (solvent); potassium sorbate (preservative); sucralose (known as Splenda™); nicotine (drug); ascorbic acid (vitamin C); alpha tocopherol (Vitamin E); vitamin B complex (e.g., vitamins B1, B2, B3, B5, B6, B12); polysaccharide gum (rheology modifier); citric acid (buffer component); food colors, and natural flavors (e.g., cherry, orange, grape, root beer, cola, spearmint and menthol). The amounts of each component may be varied. For example, the nicotine levels may provide a low-nicotine formula, or a non-nicotine formula. An example composition 26 may include: 80 weight percent (wt %) to 96 wt % water; 0.0001 wt % to 0.3 wt % nicotine; 0.0001 wt % to 0.3 wt % flavor; 0.001 wt % to 0.3 wt % buffer; 0.00001 wt % to 0.5 wt % vitamins; 1 wt % to 20 wt % sweetener; 0.001 wt % to 0.3 wt % preservative; 0.01 wt % to 5 wt % thickener; and 0.0001 wt % to 0.3 wt % colorant.

When preparing a composition 26 to be loaded into the device 10 or 110 or 210 or 310, the amount of water and thickener are varied to provide a suitable viscosity for delivery from the device 10 or 110 or 210 or 310. For instance, the viscosity of the composition 26 will vary depending on the diameter of the flow path to the user's mouth, and a highly viscous substance will difficult to inhale through a small diameter tube. The amount of flavor, sweetener and color are varied to provide pleasing organoleptic and aesthetic properties. The level of preservative is varied to provide suitable shelf life to the device 10 or 110 or 210 or 310. The amount of nicotine in the composition 26 to be loaded into the device 10 or 110 or 210 or 310 is preferably adjusted based on the interior volume of the device 10 or 110 or 210 or 310 such that 0.5 to 5.0 milligrams of nicotine are delivered to the user's mouth upon inhalation of the entire amount of composition 26 loaded into the device 10 or 110 or 210 or 310. The amount of vitamins in the composition 26 to be loaded into the device 10 or 110 or 210 or 310 can be varied up to the maximum daily recommended intake based on an expected number of uses of the device in a day.

EXAMPLES

The following examples are presented in order to further illustrate the invention. They are not intended to limit the invention in any way.

Example 1

A first non-limiting example of a composition according to the invention is shown in Table 1.

TABLE 1

|  | amount* | | grams*** | Wt. % | grams/cigarette |
|---|---|---|---|---|---|
| Water | 400 | g | 400.0000 | 69.8812% | 3.3333 |
| Cherry Flavor | 19.1 | drops** | 0.6367 | 0.1112% | 0.0053 |
| Citric Acid | 23 | drops | 0.7667 | 0.1339% | 0.0064 |
| Ascorbic Acid | 0.060 | g | 0.0600 | 0.0105% | 0.0005 |
| Splenda ™ sucralose | 38.2000 | | 38.2000 | 6.6737% | 0.3183 |
| Nicotine | 0.1200 | | 0.1200 | 0.0210% | 0.0010 |
| Potassium Sorbate | 0.764 | g | 0.7640 | 0.1335% | 0.0064 |
| Keltrol ™ xanthan gum | 7.64 | g | 7.6400 | 1.3347% | 0.0637 |
| Water | Balance | | 124.2127 | 21.7003% | 1.0351 |
|  | 572.4000 | | 572.4000 | 100.0000 | 4.7700 |

Note:
Citric acid is first prepared as a 50% (by weight) solution. [Ex. 50 g. Citric acid + 50 g. distilled water]
Sucralose is (4,1',6'-trichloro-4,1',6'-trideoxy-galactosucrose), an intense sweetener made from sucrose
*per 3 day batch
**30 drops = 1 ml.
***assuming density = 1

The first example composition is made as follows. The components are added in the order which they are listed. Make sure each ingredient is fully mixed before adding the following component. Be sure to add the Keltrol™ xanthan gum slowly, sprinkling in. It is best to use high speed blender. Viscosity can be controlled by varying the amount of Keltrol™ xanthan gum. Higher levels of Keltrol™ xanthan gum will lead to higher viscosity. Continue mixing until uniform solution is achieved. The composition 26 may then be loaded into the device 10 or 110 or 210 or 310 for use.

Example 2

A second non-limiting example of a 5 liter batch of a composition according to the invention is shown in Table 2.

TABLE 2

|  | amount | grams** | Wt. % | grams per cigarette*** |
|---|---|---|---|---|
| Water | 3846 ml. | 3846 | 76.920 | 6.92280 |
| Cherry Flavor |  | 4.009 | 0.080 | 0.00722 |
| Citric Acid* | 8.609 (50/50) | 4.3045 | 0.086 | 0.00775 |
| Ascorbic Acid |  | 2.218 | 0.044 | 0.00399 |
| Vitamin B1 | 55.51 mg. | 0.056 | 0.001 | 0.00010 |
| Vitamin B2 | 62.95 mg. | 0.063 | 0.001 | 0.00011 |
| Vitamin B3 | 740.996 mg. | 0.741 | 0.015 | 0.00133 |
| Vitamin B5 | 370.5 mg. | 0.371 | 0.007 | 0.00067 |
| Vitamin B6 | 74.1 mg. | 0.074 | 0.001 | 0.00013 |
| Vitamin B12 | 1 mg. | 0.001 | 0.000 | 0.00000 |
| Splenda ™ sucralose |  | 444.432 | 8.889 | 0.79998 |
| Nicotine | 401.234 mg. | 0.401 | 0.008 | 0.00072 |
| Potassium Sorbate |  | 4.615 | 0.092 | 0.00831 |
| Keltrol ™ xanthan gum |  | 65.382 | 1.308 | 0.11769 |
| Water | Balance | 627.33 | 12.547 | 1.12920 |
| Total |  | 5000 | 100.00 |  |

*Note: Citric acid is first prepared as a 50% (by weight) solution. [Ex. 50 g. Citric acid + 50 g. distilled water]
Sucralose is (4,1',6'-trichloro-4,1',6'-trideoxy-galactosucrose), an intense sweetener made from sucrose
**assuming density = 1
*grams per cigarette based on 9 ml./cigarette The second example composition is made as follows. The components are added in the order which they are listed. Make sure each ingredient is fully mixed before adding the following component. Be sure to add the Keltrol™ xanthan gum slowly, sprinkling in. It is best to use high speed blender. Viscosity can be controlled by varying the amount of Keltrol™ xanthan gum. Higher levels of Keltrol™ xanthan gum will lead to higher viscosity. Continue mixing until uniform solution is achieved. The composition 26 may then be loaded into the device 10 or 110 or 210 or 310** for use.

Example 3

A third non-limiting example of a 5 liter batch of a composition according to the invention is shown in Table 3.

TABLE 3

| | Amount | grams** | Wt. % | grams per cigarette*** |
|---|---|---|---|---|
| Water | 2000 | 2000.000 | 40.000 | 3.60000 |
| Cherry Flavor | | 3.608 | 0.072 | 0.00649 |
| Citric Acid* | 7.7481 | 3.874 | 0.077 | 0.00697 |
| Ascorbic Acid | | 2.883 | 0.058 | 0.00519 |
| Vitamin B1 | 72.163 mg. | 0.072 | 0.001 | 0.00013 |
| Vitamin B2 | 81.835 mg. | 0.082 | 0.002 | 0.00015 |
| Vitamin B3 | 963.2948 mg. | 0.963 | 0.019 | 0.00173 |
| Vitamin B5 | 481.65 mg. | 0.482 | 0.010 | 0.00087 |
| Vitamin B6 | 96.66 mg. | 0.097 | 0.002 | 0.00017 |
| Vitamin B12 | 1 mg. | 0.001 | 0.000 | 0.00000 |
| Splenda ™ sucralose | | 399.989 | 8.000 | 0.71998 |
| Nicotine | 456.789 mg. | 0.457 | 0.009 | 0.00082 |
| Potassium Sorbate | | 4.615 | 0.092 | 0.00831 |
| Keltrol ™ xanthan gum | | 65.382 | 1.308 | 0.11769 |
| Color | 258 mg. | 0.258 | 0.005 | 0.00046 |
| Water | Balance | 2517.237 | 50.345 | 4.53103 |
| Total | | 5000 | 100.00 | |

*Note: Citric acid is first prepared as a 50% (by weight) solution. [Ex. 50 g Citric acid + 50 g distilled water]
Sucralose is (4,1',6'-trichloro-4,1',6'-trideoxy-galactosucrose), an intense sweetener made from sucrose
**assuming density = 1
***grams per cigarette based on 9 ml./cigarette The third example composition is made as follows. The components are added in the order which they are listed. Make sure each ingredient is fully mixed before adding the following component. Be sure to add the Keltrol™ xanthan gum slowly, sprinkling in. It is best to use high speed blender. Viscosity can be controlled by varying the amount of Keltrol™ xanthan gum. Higher levels of Keltrol™ xanthan gum will lead to higher viscosity. Continue mixing until uniform solution is achieved. The composition 26 may then be loaded into the device 10 or 110 or 210 or 310 for use.

Thus, the present invention provides a device, composition, and method which facilitate the absorption of nicotine in order to reduce the incidence of tobacco smoking. The device acts as a substitute oral activity to smoking and provides a source of nicotine that reduces the withdrawal symptoms experienced when smoking is stopped.

Although the present invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A device which facilitates the absorption of nicotine in order to reduce the incidence of tobacco smoking, the device comprising:
    a tube defining an interior space, the tube having a first end with an opening and an opposite second end; and
    a moveable plug disposed in the interior space of the tube, the moveable plug structured to move toward the user's mouth and contact an inner surface of the tube upon the user ingesting from the first end; and
    a flowable liquid or gel composition disposed in the interior space of the tube, the composition including nicotine,
    wherein the composition is suitable to enter a user's mouth through the opening in the first end upon the user ingesting the composition from the first end,
    wherein the composition includes a vitamin and a flavoring agent, and
    wherein the inner surface of the tube is structured such that the plug prevents the composition from flowing around the plug when the plug is located at the second end, and
    wherein the device does not include a plunger.

2. The device of claim 1 wherein:
    the first end and the second end are each covered with a removable seal.

3. The device of claim 1 wherein:
    the amount of composition in the interior space of the tube is approximately 3 to 20 milliliters.

4. The device of claim 1 wherein:
    the amount of nicotine in the interior space of the tube is 0.5 to 5.0 milligrams.

5. The device of claim 1 wherein:
    the flavoring agent includes sucralose.

6. The device of claim 1 wherein:
    the flavoring agent includes a natural or artificial fruit flavor.

7. The device of claim 1 wherein:
    the vitamin is selected from vitamin C, vitamin E, Vitamin B, and mixtures thereof.

8. The device of claim 1 wherein:
    the flavoring agent includes a natural or artificial fruit flavor selected from cherry, orange, grape, root beer, cola, spearmint and menthol.

9. The device of claim 1 wherein:
    the tube has indicia on the first end of the tube to indicate where the user should ingest.

10. The device of claim 1 wherein:
    the second end is integral with the tube and includes at least one air hole.

11. The device of claim 1 wherein:
    the first end is covered with a mouthpiece having a frangible seal.

12. A device which facilitates the absorption of nicotine in order to reduce the incidence of tobacco smoking, the device comprising:
    a tube defining an interior space, the tube having a first end with an opening and an opposite second end; and
    a moveable plug disposed in the interior space of the tube, the moveable plug structured to move toward the user's mouth and contact an inner surface of the tube upon the user ingesting from the first end; and
    a flowable gel composition disposed in the interior space of the tube,
    wherein the composition includes nicotine and a flavoring agent, and
    wherein the composition is suitable to enter a user's mouth through the opening in the first end upon the user ingesting the composition from the first end, and
    wherein the inner surface of the tube is structured such that the plug prevents the composition from flowing around the plug when the plug is located at the second end, and
    wherein the device does not include a plunger.

13. The device of claim 12 wherein:
    the first end of the tube is covered with a mouthpiece having a frangible seal.

14. The device of claim 12 wherein:
    the composition includes a vitamin.

15. The device of claim 12 wherein:
    the amount of nicotine in the interior space of the tube is 0.5 to 5.0 milligrams.

16. The device of claim 12 wherein the composition includes:
80 wt % to 96 wt % water;
0.0001 wt % to 0.3 wt % nicotine;
0.0001 wt % to 0.3 wt % flavoring agent;
0.00001 wt % to 0.5 wt % vitamin; and
0.01 wt % to 5 wt % thickener.

17. The device of claim 12 wherein:
the composition is disposed in the interior space of the tube on a single side of the plug adjacent the opening.

18. The device of claim 1 wherein:
the composition is disposed in the interior space of the tube on a single side of the plug adjacent the opening.

19. The device of claim 12 wherein:
the first end is covered with a cap having a hole covered with a removable seal, and
the second end is covered with a cap having a hole covered with a removable seal.

20. The device of claim 1 wherein:
the first end is covered with a cap having a hole covered with a removable seal, and
the second end is covered with a cap having a hole covered with a removable seal.

* * * * *